United States Patent [19]

Richardson et al.

[11] Patent Number: 5,555,882

[45] Date of Patent: Sep. 17, 1996

[54] METHOD AND APPARATUS FOR REDUCING AMBIENT NOISE EFFECTS IN ELECTRONIC MONITORING INSTRUMENTS

[75] Inventors: Charles A. Richardson, San Francisco; Michael Bernstein, San Ramon; Jerry K. Okikawa, Oakland; Terrence R. Bennett, Richmond, all of Calif.

[73] Assignee: Nellcor Incorporated, Pleasanton, Calif.

[21] Appl. No.: 295,349

[22] Filed: Aug. 24, 1994

Related U.S. Application Data

[63] Continuation of Ser. No. 965,684, Oct. 23, 1992, Pat. No. 5,368,224.

[51] Int. Cl.$^6$ .......................................................... A61B 5/00
[52] U.S. Cl. ............................................... 128/633; 356/41
[58] Field of Search ..................................... 128/633, 664, 128/665, 666; 356/39, 40, 41

[56] References Cited

U.S. PATENT DOCUMENTS

| | | |
|---|---|---|
| 4,086,915 | 5/1978 | Kofsky et al. . |
| 4,819,752 | 4/1989 | Zelin ........................................ 128/633 |
| 4,863,265 | 9/1989 | Flower et al. . |
| 4,867,571 | 9/1989 | Frick et al. ............................... 356/436 |
| 5,040,539 | 8/1991 | Scmitt et al. ............................. 128/633 |
| 5,190,038 | 3/1993 | Polson et al. ............................ 128/633 |
| 5,193,543 | 3/1993 | Yelderman ............................... 128/633 |
| 5,203,329 | 4/1993 | Takatani et al. ......................... 128/633 |
| 5,246,002 | 9/1993 | Prosser .................................... 128/633 |
| 5,349,952 | 9/1994 | McCarthy et al. ....................... 128/633 |

FOREIGN PATENT DOCUMENTS

| | | |
|---|---|---|
| 0102816 | 8/1983 | European Pat. Off. . |
| 0261789 | 8/1987 | European Pat. Off. . |
| 0271340 | 12/1987 | European Pat. Off. . |

Primary Examiner—Angela D. Sykes
Assistant Examiner—Eric F. Winakur
Attorney, Agent, or Firm—Townsend and Townsend and Crew LLP

[57] ABSTRACT

The present invention provides a method and apparatus for adapting to noise sources affecting a pulse oximeter. Various available frequencies are evaluated to determine their respective noise levels and one is selected to act as the operating demultiplexer frequency. During normal operation of the pulse oximeter, the various available demultiplexer frequencies are periodically scanned to determine which has the lowest associated noise. The noise level associated with the operating frequency is used to determine the signal-to-noise ratio of the pulse oximeter signals and thereby qualify certain signals from the pulse oximeter. Those pulses associated with a signal-to-noise ratio below a predetermined threshold are rejected and excluded from use in calculating blood oxygen saturation.

7 Claims, 3 Drawing Sheets

METHOD AND APPARATUS FOR REDUCING AMBIENT NOISE EFFECTS IN ELECTRONIC MONITORING INSTRUMENTS

This is a continuation of application Ser. No. 07/965,684 filed Oct. 23, 1992, now U.S. Pat. No. 5,368,224.

BACKGROUND

This invention relates to a method and apparatus for detecting and reducing the effects of ambient electromagnetic noise (including photic noise) on electronic instruments, particularly on electronic physiological monitoring instruments such as pulse oximeters.

The number of different kinds of electronic instruments used in hospitals, and the number of all electronic instruments of all kinds in use at any given time in each hospital, are on the rise. Besides performing its intended function, each instrument emits electromagnetic radiation at frequencies and intensities governed by the configuration of its electronic circuitry and the manner in which the instrument is used. For some instruments, such as radio telemetry monitors, the emission of electromagnetic radiation is the instruments' primary function.

In addition, superimposed on the electromagnetic radiation emitted by the instruments is the electromagnetic radiation emitted by the room lights and the A.C. power supply. In each room of the hospital, these electronic emissions combine to provide a complex background noise level whose instantaneous frequency and intensity characteristics depend on room lights, room power, and the nature of the instruments in use at any particular time. The effect of this background noise on the operation of an electronic instrument depends on the nature of the instrument. The use of a pulse oximeter in a noisy environment is a good example.

The principles of pulse oximetry and the operation of commercially available pulse oximeters are well known in the art. For example, the sensor of the pulse oximeter system described in U.S. Pat. No. 4,653,498 and U.S. Pat. No. 4,869,254 (both of which are incorporated herein by reference for all purposes) emits light alternately at a red and at an infrared wavelength into the patient's tissue, and a single photodetector senses the light transmitted through the tissue at each wavelength. The time-varying photodetector output represents the transmitted red and infrared signals separated by "dark" periods during which no light is emitted by the sensor. A demultiplexer synchronized with the sensor's red and infrared light sources separates the red and infrared portions of the photodetector output for further processing by the oximeter.

The physiological parameter measured by pulse oximeters is arterial blood oxygen saturation. The light-absorptive properties of blood at red and infrared wavelengths vary with the relative concentrations of oxyhemoglobin and deoxyhemoglobin in the blood. The portions of the photodetector output used in the oxygen saturation calculation, therefore, are the changes in red and infrared light transmission caused by the pulsatile changes in arterial blood volume at the sensor site. These pulse to pulse changes in transmitted light level are small in comparison to the overall intensity of the transmitted light, on the order of 1–3%, and are very susceptible to the influence of background noise.

The output of electric lights varies at a frequency related to the frequency of the A.C. power supply and its harmonics. If any frequency, fundamental or harmonic, of the ambient light variations match or are close to any frequency, fundamental or harmonic, of the oximeter's multiplexed light source, and if ambient light somehow reaches the photodetector, the oximeter may not be able to distinguish between the photodetector output related to red and infrared light sources (i.e., the signal) and the photodetector output related to ambient light (i.e., the noise). The red and infrared light are therefore typically multiplexed (and the photodetector synchronously demultiplexed) at frequencies other than room light frequencies. See, e.g., U.S. Pat. No. 4,653,498.

There are, however, many other sources of electromagnetic radiation in the pulse oximeter operating environment, including ECG monitors, impedance apnea monitors, isolation power supplies in other monitoring instruments, and electrocautery tools, each with its own characteristic operating frequencies. It would be difficult, if not impossible, to select an oximeter synchronous demultiplexer frequency that would not be affected by at least one of the potential noise sources in the oximeter's operating environment.

One prior art approach to this problem is to add a low-pass filter at the photodetector output to remove portions of the photodetector output signal above a certain frequency, say 100 to 300 kHz. See, e.g., U.S. Pat. No. Re. 33,643. This filter would not remove the effects of noise at the oximeter's synchronous demultiplexer frequency, however.

What is needed, therefore, is a way to reduce the effects of ambient electromagnetic noise in electronic monitoring instruments, especially when the noise source frequency (or a harmonic of the noise source frequency) is approximately the same as the fundamental frequency or harmonics at which the instrument is operating.

SUMMARY OF THE INVENTION

The present invention provides a method and apparatus for adapting to noise sources affecting electronic monitoring instruments. Various available frequencies (discrete or continuous) are evaluated to determine their respective noise levels and one is selected to act as the operating demultiplexer frequency. Then during normal operation of the instrument, the various available demultiplexer frequencies are periodically scanned to redetermine which has the lowest associated noise. This frequency agility allows the instrument to shift from a first multiplexing frequency to another in order to avoid noise appearing at the first multiplexing frequency. In some embodiments, as many as 1000 frequency channels are available.

These techniques allow the invention to adapt to the total noise found in a given environment, such as a hospital. Thus, the present invention can be used in different locations having different noise sources. It can also be used in a single location to adapt to noise changes occurring over time. Because the instrument can measure and report noise, it allows users to rapidly adjust sensors to obtain a good signal and detect interfering noise sources.

Preferably, the method and apparatus of the present invention are used to process photodetection signals obtained with a pulse oximeter. To monitor the noise in the oximeter signal at a given frequency, the oximeter is preferably operated in the "dark." In other words, the oximeter light sources (typically Light Emitting Diodes "LEDs") are turned off while the oximeter continues to monitor the detector signal at the selected frequency. Thus, the noise associated with ground loops, radio telemetry monitors, and all other sources in the environment is detected and quantified free of contributions from the physiological pulse information. The noise level so obtained can be used to rate a selected frequency and to assess the signal-to-noise ratio of subsequently taken physiological signals. Because noise levels are measured in situ, the oximeter may conserve power by reducing LED drive current while maintaining a safe signal-to-noise ratio.

Thus, one aspect of the present invention is a method and apparatus for identifying a pulse oximeter demultiplexing frequency at which the contribution of noise to the signal is relatively low. To accomplish this a plurality of multiplexing frequencies are evaluated to determine which is quietest. That frequency is then adopted for use during collection of blood oxygen saturation data. If, during operation, a source of noise is introduced that interferes with the "adopted" demultiplexing frequency, the oximeter searches for a new, quieter, demultiplexing frequency. If one is located, the oximeter then shifts to that frequency.

Another aspect of the present invention involves a method and apparatus for "qualifying" optical pulses detected by a pulse oximeter. Those pulses associated with a signal-to-noise ratio below a predetermined threshold are rejected and excluded from further use by the pulse oximeter monitor, while qualified pulses are available for use in calculating blood oxygen saturation.

The noise values used to approximate the signal-to-noise ratio may be obtained from various sources. For example, the "dark" noise level used to select the demultiplexer frequency can be used. In addition (or alternatively), the physiological signal can be passed through a high pass filter to determine the power associated with the higher frequencies, which approximate the total noise in the signal.

A further understanding of the present invention may be obtained by reference to the following discussion and associated drawings.

DESCRIPTION OF THE PREFERRED EMBODIMENTS

A preferred embodiment of this invention will be described as implemented in electronic physiological monitoring instruments, in particular, a pulse oximeter. For purposes of this description, noise is defined as the measured signal variations about a mean apart from any signal due to the measured physiological parameter.

Figure 1:
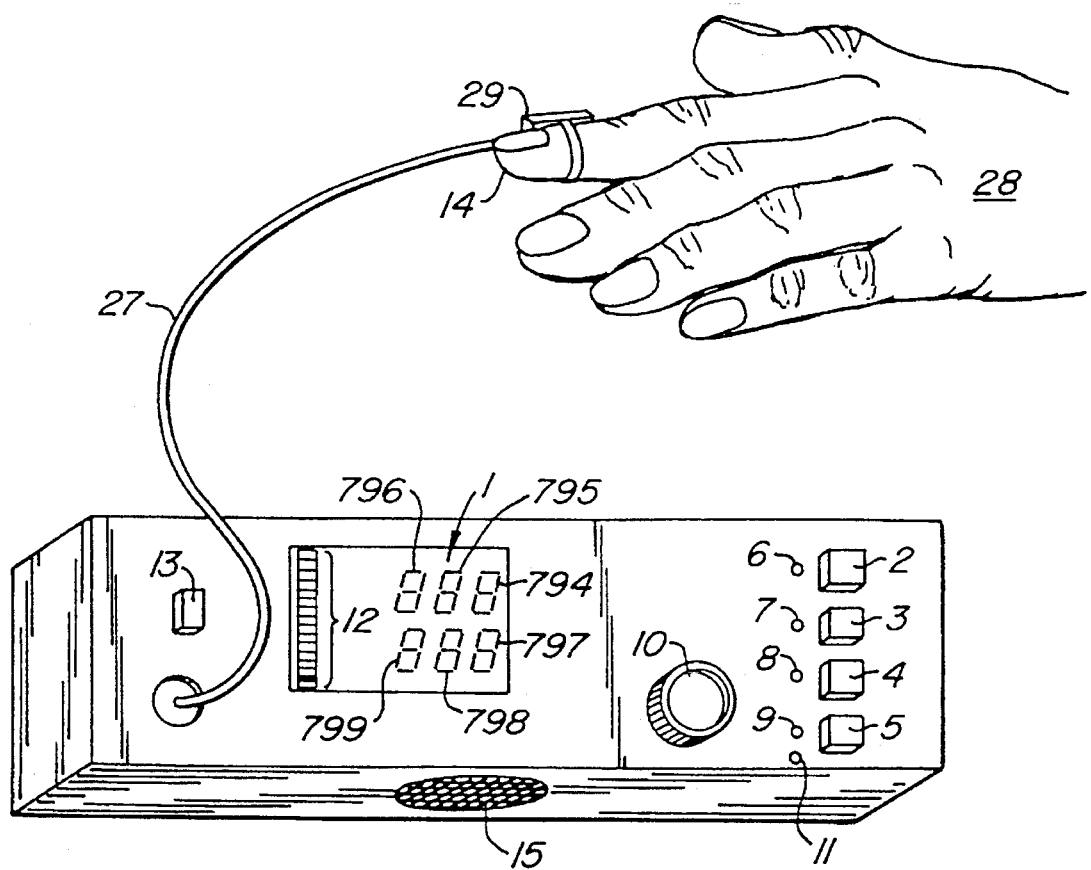
FIG. 1 is a perspective view of the instrument of this invention illustrating the instrument housing and attachment of a sensor to the finger of a patient.

Referring to FIG. 1, a pulse oximeter instrument housing 26 suitable for use with the present invention is illustrated. Outwardly, the housing includes a digital display 1, circuitry select button array 2 through 5, alarm status lights 6 through 9, an optically coupled adjustment knob 10, sync status light 11, LED digital viewmeter 12, and power switch 13. A speaker 15 is placed under the instrument housing.

From a connector (not shown) in housing 26 there extend wires 27 to a detector probe 29. Detector 29 is placed upon the finger 14 of a patient 28. Utilizing the placement of the detector 29 at the finger 14, all of the readings in this invention are made possible. In a typical pulse oximeter, a first light emitting diode in the red range (e.g. 660 nanometers) and a second light emitting diode in the infrared range (e.g. 940 nanometers) are sequentially pulsed to emit light.

A clock controls the sequential output of light from the light emitting diodes and to a duty cycle of at least 1 in 4. Reception of a red signal occurs during two of the four time periods and reception of an infrared signal occurs during the other two time periods. One time cycle for each of the two wavelengths is a "dark" cycle. In other words, the LED is turned off and only ambient light is detected. The dark signal is "subtracted" from the LED signal, thus, improving the signal-to-noise ratio of the pulse oximeter. Subtraction is performed by switching on an inverter each time the dark signal is received. This inverted signal is then combined with the preceding LED signal (uninverted) to decrease the effects of ambient light. This works fine for light of constant intensity. However, time varying light sources at harmonics of the AC mains still contribute to baseband noise when the harmonics occur near harmonics of the synchronous demultiplexer.

In the preferred embodiment of this invention, the pulse oximeter selects its synchronous demultiplexer frequency $f_{TMUX}$ from a ranked list of possible frequencies $f_N$. The available frequencies $f_N$ are ranked empirically by (1) identifying noise sources in the range of possible $f_{TMUX}$ values; (2) determining, for each noise source, the degree of interference caused by the noise source within that range; (3) selecting N possible $f_{TMUX}$ frequencies that do not coincide or approximate the frequencies of the identified noise sources; and (4) ranking the chosen frequencies according to an increased degree of interference from the expected noise, with $f_1$ being the least likely $f_{TMUX}$ frequency to be affected by noise from the operating environment. Typically, the available frequencies $f_N$ are scanned until a downward trend in noise is detected. When the trend reverses, the frequency with the lowest noise is adopted as $f_{TMUX}$. Of course, other methods for scanning the possible frequencies can be used. For example, every available frequency can be checked, and the one having the lowest noise value is adopted as $f_{TMUX}$. In preferred embodiments, the $f_N$ values are stored in ROM (read-only memory) in the pulse oximeter. Typically, the available frequencies will be between about 200 and about 3000 Hz, and preferably between about 1500 and 2500 Hz.

In preferred embodiments, the available values of $f_{TMUX}$ are selected to minimize the problem specifically caused by A.C. mains harmonics (from e.g. 50 or 60 Hz photic sources) being "aliased" down to the analog passband. This occurs when an A.C. fundamental frequency or harmonic thereof differs from the demultiplexer frequency by an amount corresponding to a frequency in the passband. For example, if the A.C. main has a fundamental frequency at 50 Hz and the demultiplexer is operated at 2025 Hz, an aliased 25 Hz signal is produced. This falls outside the range of a 0–20 Hz passband used in a typical pulse oximeter. However, the second harmonic of the demultiplexer fundamental is 4050 Hz, which falls right on a harmonic of the A.C. main, thus producing an aliased signal in the physiological frequency range, i.e. 0–5 Hz. The oximeter has no way of gauging the contribution of this "noise" to physiological signal.

To deal with this problem, values of $f_{TMUX}$ are purposely chosen to be somewhat close to a harmonic of the A.C. mains. In many embodiments, the $f_{TMUX}$ available frequencies are separated by at about 10–15 Hz from the frequency of the A.C. power supply and harmonics thereof. Thus, the aliased signal shows up in the analog passband, but is far enough from the physiological frequency range that it can easily be identified as noise. This serves two purposes. First, the noise spike at 10–15 Hz serves as a "marker" indicating the relative power of the A.C. power line noise that ultimately folds back into the physiological signal (possibly at the fifth or sixth harmonic of the demultiplexer fundamental). Second, the power of the power line noise that folds back into the physiological frequencies can be expected to be relatively weak. For example, if the fundamental of the demultiplexer is 10 Hz away from a harmonic of a power line, the second harmonic is 20 Hz away, the third is 30 Hz away, and so on until the fifth or sixth harmonic which falls on or close to a harmonic of the power line. However, if the demultiplexer fundamental is in the range of 2000 to 3000 Hz, the fifth and sixth harmonics are at 10 kHz or greater, a region in which the noise power from the A.C. mains rapidly falls off.

In preferred embodiments, the noise at the available demultiplexer frequencies is evaluated when the red and/or infrared light source of the pulse oximeter sensor is turned off. By turning the LEDs off, the oximeter becomes a passive monitor, listening to signals which come from foreign sources like body impedance monitors, AC power lines, electrocautery, etc. The signal so measured will provide a good measure of the noise level at the selected frequency.

It should be noted that a pulse oximeter in its normal operating mode is an "active" signal sensor. This means that the oximeter supplies energy to the system being studied (i.e. tissue having blood flow) and the system modulates the supplied energy to provide information. The techniques of the present invention can generally be applied to any active signal sensing monitor. Thus, for example, the present invention can be employed in tissue impedance techniques such as respiratory monitoring, cardiac output monitoring, and apnea monitoring. These techniques pass energy in the form of electrical current through the body so that the tissue impedance, modulated by mechanical events of the body (breathing lungs or beating heart) can be monitored. Other examples of active signal sensing devices include spectral gas monitors such as some carbon dioxide monitors.

Figures 2, 4:
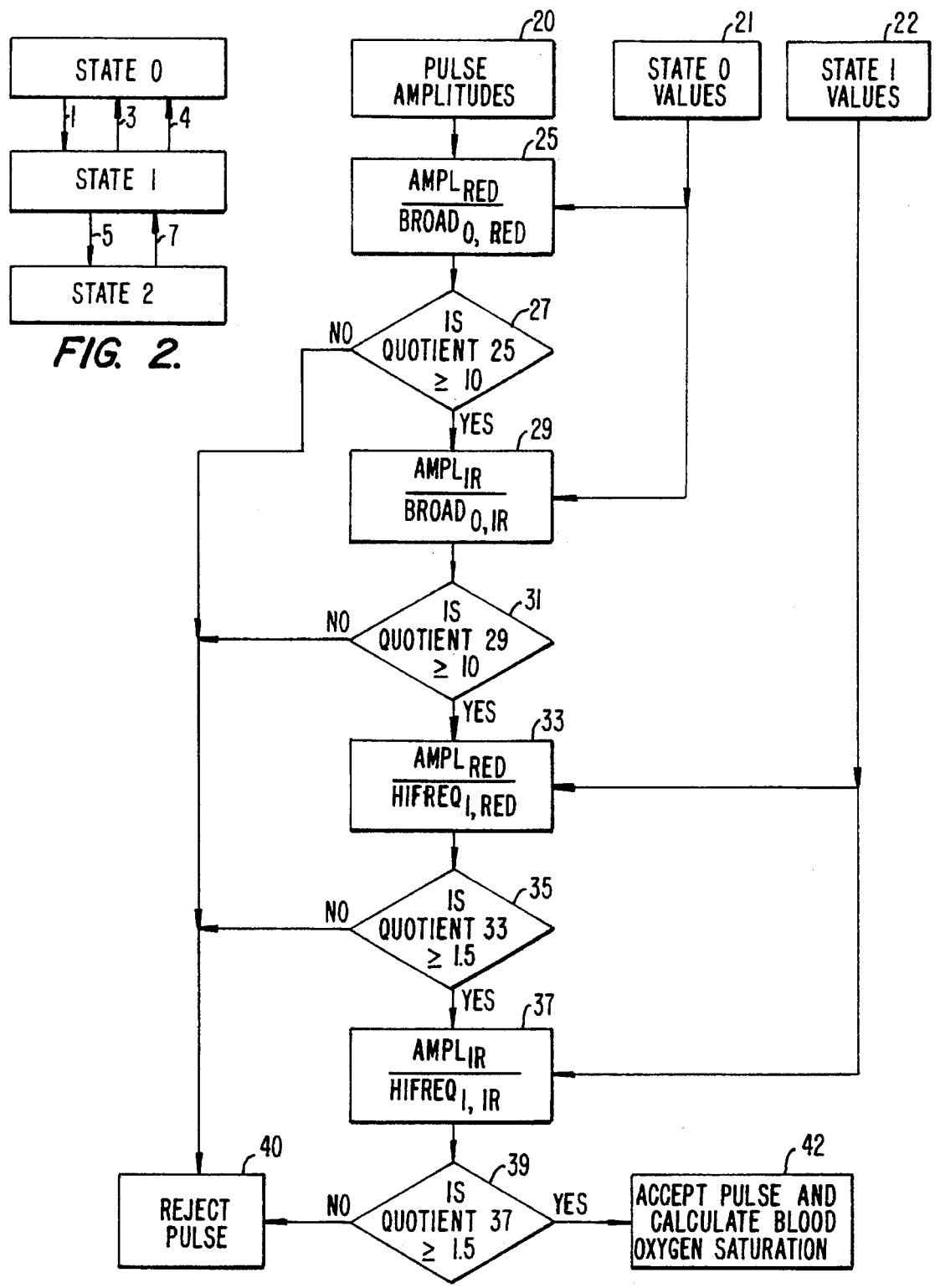
FIG. 2 is a flow chart showing the processes connecting the three states of the present invention.
FIG. 4 is a flow diagram of a pulse qualification procedure of the present invention.

Referring now to FIG. 2, the method of the preferred embodiment (as implemented in a pulse oximeter) operates in three states or modes: State 0, State 1, and State 2. When the pulse oximeter is first powered up, it is in State 0. In State 0, the oximeter does not provide power to the sensor's LEDs but collects a digitized "signal" from the sensor's photodetector in the red and infrared channels. The oximeter uses State 0 to read the ambient noise (both electrical and photic) in the absence of any physiological signal provided by illumination of the patient's tissue by the LEDs and to select an initial $f_{TMUX}$. In this state, the oximeter cannot determine saturation values, but it can determine noise as a passive monitor. The initial $f_{TMUX}$ is selected on the basis of its quietness from among a group of available frequencies.

When $f_{TMUX}$ is settled on in State 0, the system moves to State 1, (process 1) where both LEDs are turned on and the blood oxygen saturation is monitored. According to a predefined schedule, the system periodically reverts from State 1 to State 0 (process 3) to reassess the noise at $f_{TMUX}$, and, if necessary, find a new $f_{TMUX}$. While in State 1, the system continually monitors high frequency noise in the active signal and qualifies the physiological signal based on its signal-to-noise ratio. Unqualified signal pulses are not used to calculate blood oxygen saturation. Also, if the system determines that the signal-to-noise ratio at $f_{TMUX}$ decreases below an acceptable level, it moves to State 0 (process 4) to search for a new $f_{TMUX}$.

The system frequently moves from State 1 to State 2 (process 5) to reassess the noise at $f_{TMUX}$. This is accomplished by turning off one LED; typically the red LED. (In comparison, State 0 turns off both LEDs.) In State 2, the pulse oximeter cannot calculate blood oxygen saturation, but it can monitor pulse rate and otherwise give the appearance of operating normally. After the noise is assessed in State 2, the system returns to State 1 (process 7) and operates normally, employing the new noise level calculated in State 2.

Figure 3:
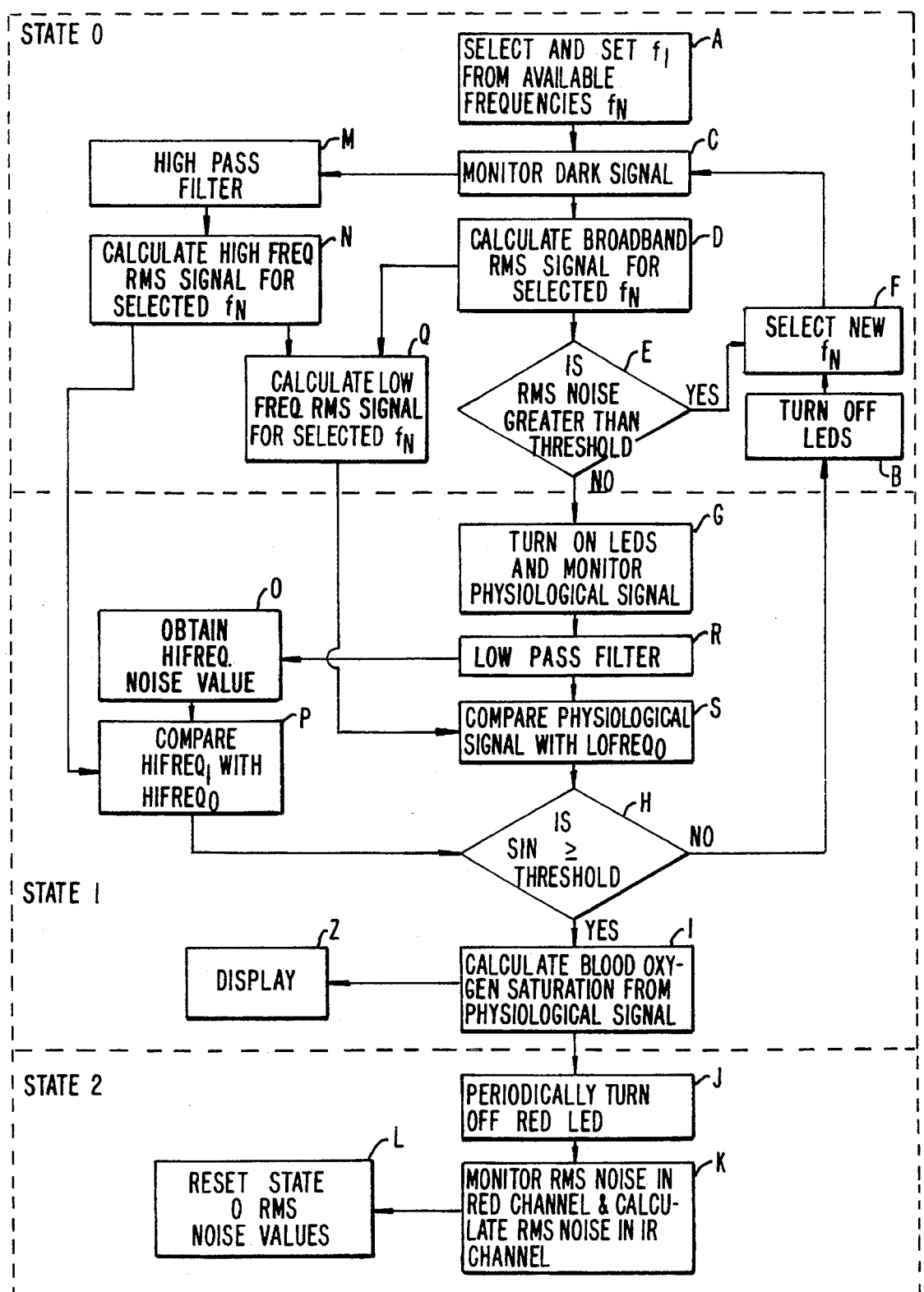
FIG. 3 is a flow diagram of a method employed to determine noise levels at demultiplexing frequencies.

The root-mean-square ("RMS") value of noise in State 0 is computed by estimating the mean signal level, subtracting the mean signal from the instantaneous signal, squaring the difference, summing the squared values over the measurement epoch, and taking the square root of the value. FIG. 4 is a flow chart that includes the State 0 broadband noise algorithm used by the pulse oximeter in State 0. It should be understood that while the flow chart shows signals read and calculations performed in only one channel, the oximeter uses this algorithm essentially simultaneously in both the red and infrared channels. As shown in FIG. 3, the synchronous frequency f is set to $f_1$ when the oximeter enters State 0 (Step A). The oximeter then starts reading values (Step C). To calculate the RMS dark noise for $f_1$ (or any $f_N$ in Step D), the oximeter's microprocessor begins by reading a first detector output value $x_1$ and stores this value as SUM in the oximeter's memory. The microprocessor then reads a second value $x_2$, adds it to SUM and divides the total by 2 to compute MEAN. After computing the mean, the microprocessor determines the differences between $x_2$ and MEAN, squares the difference, and stores this value as SUMSQ in memory. The values of $x_i$ are read from both the red and infrared channels of the oximeter at the times when the red and infrared LEDs would be lit if the oximeter were in its operating state.

The microprocessor then compares SUMSQ values with threshold THRESH, which is set initially at $T_{INIT}$, an arbitrary value based on the inherent noise tolerance of the instrument. If both $SUMSQ_{RED}$ and $SUMSQ_{IR}$ are less than THRESH, then the microprocessor reads a third detector value $x_3$ (in both the red and infrared channels), adds $x_3$ to SUM, determines the difference between $x_3$ and MEAN, squares the difference and adds the squared value to SUMSQ.

The microprocessor once again compares the SUMSQ values to THRESH. If both SUMSQ values are still less than THRESH, then the microprocessor reads a fourth detector value $x_4$, adds $x_4$ to SUM, and computes a new value of MEAN. The microprocessor then determines the difference between $x_4$ and MEAN, squares the difference and adds the squared value to SUMSQ.

The process repeats for 65 values of $x_i$, as long as both $SUMSQ_{RED}$ and $SUMSQ_{IR}$ are less than THRESH. New values of MEAN are computed after gathering $x_8$, $x_{16}$, $x_{32}$ and $x_{64}$, i.e., whenever i is a power of 2. In the preferred embodiment, the time to gather and process $x_{1-65}$ takes approximately 1 second, based on an oximeter digital sampling rate of 57 Hz. $SUMSQ_{RED}$ and $SUMSQ_{IR}$ are both divided by 64 and the quotients are raised to the one-half power to give the RMS noise in Step D. If both SUMSQ values remain below THRESH for all 64 points (Step E), then the microprocessor changes the value of $THRESH_{RED}$ to $SUMSQ_{RED}$ and $THRESH_{IR}$ to $SUMSQ_{IR}$ and stores $f_1$ as the value of $f_{TMUX}$.

The oximeter then enters State 1 (Step 6) where the LEDs begin emitting light pulses and the microprocessor monitors the physiological signal at $f_1$. From the detected physiological signal, the microprocessor calculates the current blood oxygen saturation (Step I) using conventional methods. All the while, the signal-to-noise ratio of the physiological signal at $f_1$ is monitored, and, if the ratio falls below a predetermined threshold (Step H), the system reenters State 0 (Step F) to determine whether $f_2$ yields a lower broadband noise total in both channels than $f_1$ had. If so, then the microprocessor updates the THRESH values, stores $f_2$ as $f_{TMUX}$, and reenters State 1. If not, then the microprocessor looks for another frequency $f_N$ having a lower broadband noise total. If none is found, the microprocessor uses the previously stored $f_{TMUX}$ value when it enters State 1.

In alternative embodiments, the system will determine the noise associated with multiple values of $f_N$ stored on the ROM before selecting $f_{TMUX}$ and reentering State 1 to detect the physiological signal. In such systems, the detector will remain in State 0 until the frequency with the lowest noise is identified. If none of the ranked values of possible frequencies passes this State 0 test, the instrument displays an error message and will not operate.

A parallel computation of State 0 high frequency noise is performed by the microprocessor in both the red and infrared channels. As the microprocessor reads the red and infrared $x_i$ values for use in the routine of FIG. 3, it passes the $x_i$ values through a high pass filter (Step M) having a cutoff of 7 Hz to yield filtered values $y_i$. The sum of the squares of the $u_i$ values is computed as $SUMSQ_{HI}$.

The red and infrared values of SUMSQ from the last State 0 calculation are measurements of the broadband noise in the red and infrared channels, respectively. As noted above, microprocessor computes State 0 broadband noise values $BROAD_{0,RED}$ and $BROAD_{0,IR}$ as the square root of SUMSQ/64 (Step D). Similarly, the microprocessor computes State 0 high frequency noise values $HIFREQ_{0,RED}$ and $HIFREQ_{0,IR}$ as the square root of $SUMSQ_{HI}/64$ (Step N). Finally, the microprocessor computes State 0 low frequency noise values $LOFREQ_{0,RED}$ and $LOFREQ_{0,IR}$ (Step Q) as follows:

$$LOFREQ_{0,RED}^2 = BROAD_{0,RED}^2 - HIFREQ_{0,RED}^2$$

$$LOFREQ_{0,IR}^2 = BROAD_{0,IR}^2 - HIFREQ_{0,IR}^2$$

The microprocessor uses these values in addition to the standard qualification tests to qualify the incoming physiological signal in State 1, as discussed below.

Because noise sources in the oximeter environment may vary periodically, and possibly interfere with a previously quiet $f_{TMUX}$, the system should occasionally revert to State 0. Thus, it can be redetermined whether the RMS noise $f_{TMUX}$ is still within the threshold. In a preferred embodiment, the microprocessor reverts to State 0 30 seconds after the end of the initial State 0 routine, 1 minute after the end of the second State 0 routine, 5 minutes after the end of the third State 0 routine, then 15 minutes after the end of each subsequent State 0 routine.

State 1 is the oximeter's normal operating state. The LEDs are activated alternately at a frequency of $f_{TMUX}$, and the microprocessor uses the same $f_{TMUX}$ frequency to distinguish the photodetector signal corresponding to the red LED from the photodetector signal corresponding to the infrared LED. While in State 1, the noise values calculated in State 0 are compared to the pulse signals (Steps P and S). The pulse oximeter operating in the normal mode (i.e. State 1) in a relatively noise free environment has good internal estimates of the signal level in both optical channels, the pulse amplitudes. The ratio of the signal, as measured by pulse amplitudes during normal operating mode with the LEDs turned on, to the noise, measured with the LEDs turned off and scaled appropriately for internal gains, serves as one criterion for acceptable signals. This will be an accurate estimate of the signal-to-noise ratio when the noise measurement epoch and the signal measuring epoch are close in time and an appropriate measurement when the pulse oximeter is rapidly changing $f_{TMUX}$ and estimating noise to select an optimal value for $f_{TMUX}$. Once that selection has been made, however, the oximeter must be able to monitor the signal-to-noise ratio continuously.

Thus, in addition, a continuous estimate of nonphysiologic noise is computed and compared with the pulse signals. An approximation for a continuous signal-to-noise ratio may be the ratio of power in the physiological passband [0.5, 5 Hz] to the power in the nonphysiological passband [8, 20 Hz]. In a preferred embodiment, the red and infrared analog outputs of the synchronous demultiplexer go into low pass analog filters (Step R), and the outputs of the filters are digitally sampled at 57 Hz. The digital signals then pass through a high pass filter at 7 Hz to derive State 1 high frequency noise values $HIFREQ_1$ (Step O) for the red and infrared channels. The squares of each value from the red and infrared high pass filters are stored in 64 point circular buffers. When a pulse is detected using a pulse detection algorithm (such as in the Nellcor Incorporated model N-200 pulse oximeter), the microprocessor sums the 64 points in the circular buffers, divides by 64 and takes the square root to derive $HIFREQ_{1,RED}$ and $HIFREQ_{1,IR}$ for the two optical channels. These noise measurements made in State 1 are less robust than those of State 0 because only high frequency noise can be estimated and detected, but the estimates are available for testing every detected pulse.

Preferred pulse oximeters employ timeout alarms to alert the user when no pulses are detected and qualified during an arbitrary time period. In the Nellcor N-200 pulse oximeter, this arbitrary period is 10 seconds. This invention adds a noise criteria failure timeout as follows. If the pulse is not sufficiently greater than the noise (Step H), it is rejected and no saturation is computed. If several pulses are rejected (e.g. after about 5 seconds), the noise state reverts to State 0 and a new estimate of the noise is computed. If, on the other hand, the pulse is sufficiently greater than the noise, a new saturation is calculated and displayed (Steps I and Z). Periodically in State 1 the state is forced to State 2. Note that in State 1, the oximeter is functioning normally and saturation values are presented to the clinician for each detected and accepted pulse.

If pulses fail to pass the noise qualification tests for five seconds (or other suitable period), the oximeter moves from State 1 to State 0.

In preferred embodiments, various additional tests are conducted on the pulse signal obtained in State 1. For example, the continuous high frequency noise measured in State 1 (State 0) is frequently compared with the State 0 high frequency noise values $HIFREQ_{0,RED}$ and $HIFREQ_{0,IR}$ (Step P) because the noise at $f_{TMUX}$ may suddenly change during normal operation. If so, the state returns to State 0 where a new $f_{TMUX}$ is determined. In addition, the physiological signal is compared with the State 0 low frequency noise values $LOFREQ_{0,RED}$ and $LOFREQ_{0,IR}$ (Step S) to provide an estimate of the relative signal and noise power in the physiological bandpass.

Prior pulse oximeters (such as the Nellcor N-200) use a set of pulse qualification tests to accept or reject detected pulses. The present invention adds four new tests to these prior art qualification tests (as shown in FIG. 4 and lumped into Step H and FIG. 3). In general, these new tests set signal-to-noise thresholds, where the pulse amplitudes are the "signals" and the noise parameters are as defined above. As shown in FIG. 4, the pulse amplitudes 20 are compared with State 0 broadband values 21 and State 1 high frequency values 22 at 25, 29, 23 and 37. Pulse qualification tests 27, 31, 35, and 39 are performed to determine whether the pulse is rejected 40 or accepted 42. In the preferred embodiment, the noise qualification tests are as follows:

$$\frac{AMPL_{RED}}{BROAD_{0,RED}} \geq 10$$

$$\frac{AMPL_{IR}}{BROAD_{0,IR}} \geq 10$$

$$\frac{AMPL_{RED}}{HIFREQ_{1,RED}} \geq 1.5$$

$$\frac{AMPL_{IR}}{HIFREQ_{1,IR}} \geq 1.5$$

If any of these criteria are not met, the detected pulse is rejected. In the preferred embodiment, the microprocessor performs these new tests only after the detected pulses have passed the prior art pulse qualification tests. It should be understood, however, that these noise threshold tests may be performed before, during, after or completely independent of any other pulse qualification tests without departing from the spirit of this invention. The oximeter treats a failure of any of these State 1 noise tests the same as failure of any of the standard pulse qualification tests, i.e., by disqualifying the pulse.

In some embodiments, the method also includes steps of displaying blood saturation values calculated from accepted values, maintaining a display of the most recent blood saturation value when a pulse is rejected, and then updating the displayed value whenever an accepted pulse is used to calculate blood saturation.

Every 30 seconds, the pulse oximeter enters noise State 2. The purpose of State 2 is to detect new noise sources that may have appeared since the last State 0 noise measurements by turning off the red LED (Step J) and measuring ambient noise in the red channel only (Step K). Since the infrared channel is still operating, the pulse oximeter can maintain its pulse waveform display, heart rate estimates, and audible pulse tone, so long as the infrared pulses meet the qualification criteria. In addition, since State 2 is of relatively short duration, the pulse oximeter may continue to display the last computed oxygen saturation number throughout State 2 even though no new saturations numbers can be computed.

In State 2, the red LED is turned off for approximately 1.4 seconds. Using the State 0 noise computations for the red channel only, the microprocessor computes new noise values: $BROAD_{2,RED}$, $HIFREQ_{2,RED}$ and $LOFREQ_{2,RED}$. The microprocessor then uses these values to estimate new State 0 values (Step L). For the red channel State 0 value estimates, the microprocessor scales the measured values by a ratio of the working (i.e., State 1) gain to the gain value used in State 0. For the infrared channel State 0 value estimates, the microprocessor scales the newly estimated red channel values by the ratio of the infrared to red channel gains. The pulse oximeter then returns to State 1 and uses the newly estimated State 0 values in the pulse qualification tests.

In some preferred embodiments, the signal, noise and ratios are computed for the IR channel as well as the red channel as an additional precaution. However, if the oximeter has insufficient idle time, these values are computed on the red channel only because the noise in the red channel is greater than or equal to the noise in the infrared channel under practical conditions.

Most of the above methods can be implemented by modifying the software controlling existing pulse oximeters such as the N-200 of Nellcor, Incorporated. In alternative embodiments, the active signal sensing monitor (e.g. a pulse oximeter) employs an additional "hardware" channel multiplexed to the monitor signal when no energy sources are on. For typical pulse oximeters, this "dark channel" exist as a third channel in addition to the red and infrared channels. Of course, other instruments such as apnea monitors having only a single signal channel will have now have two channels by the introduction of the dark channel. The dark channel allows continuous monitoring of noise for rapid response to a changing noise environment. Thus, the need to periodically revert to State 0 or State 2 as described above is minimized or eliminated. However, to provide an accurate assessment of noise, the additional channel requires an analog filter chain having the same noise characteristics as the red and IR channels.

Conclusion

As will be understood with those familiar with the art, the present invention may be embodied in other specific forms without departing from the spirit or essential characteristics thereof. For example, the signal-to-noise thresholds used in pulse qualification tests could be varied. In addition, the particular cutoff frequencies for low-pass filters could be adjusted. Accordingly, the disclosure of the preferred embodiment of the invention is intended to be illustrative, but not limiting of the scope of the invention, which will be set forth in the following claims.

What is claimed is:

1. A pulse oximeter comprising:
   (a) a sensor including two light sources and a photodetector, the two light sources alternately generating light pulses which pass through a patient's skin to produce attenuated optical signals monitored by the photodetector;
   (b) a demultiplexer coupled to the sensor for separating the attenuated optical signals from the two light sources, the demultiplexer and the light sources operating at an adjustable selected demultiplexing frequency;
   (c) a ROM having a plurality of available frequencies recorded;
   (d) a first processor coupled to the demultiplexer and the ROM for periodically determining the noise associated with the available frequencies, the first processor selecting, and adjusting if necessary, the adjustable selected demultiplexing frequency; and
   (e) a second processor coupled to the sensor for periodically determining the patient's blood oxygen saturation from the optical signals monitored by the photodetector.

2. The pulse oximeter recited in claim 1 wherein the available frequencies are separated by at least 10 Hz from 50 to 60 Hz and harmonics thereof.

3. The pulse oximeter recited in claim 1 wherein the available frequencies are between about 1500 and 2500 Hz.

4. The pulse oximeter recited in claim 1 wherein the first processor includes means for periodically determining the root-mean-square noise associated with the attenuated optical signals for each available frequency and selecting the available frequency for which the attenuated optical signals have the lowest root-mean-square noise as the adjustable selected demultiplexing frequency.

5. The pulse oximeter recited in claim 4 further comprising a third processor calculating a signal-to-noise ratio from the root-mean-square noise associated with the attenuated optical signals, the third processor preventing the second processor from determining the patient's blood oxygen saturation when the attenuated optical signals have a signal-to-noise ratio below a predetermined value.

6. The pulse oximeter recited in claim 1 wherein the lights sources are red and infrared LEDs.

7. The pulse oximeter recited in claim 1 wherein the first processor determines the noise associated with the available frequencies while at least one of the two light sources is not generating light pulses.

* * * * *